(12) United States Patent
Sheng

(10) Patent No.: US 8,858,953 B2
(45) Date of Patent: Oct. 14, 2014

(54) HERBAL COMPOSITION FOR TREATING CANCER

(76) Inventor: Yu-Hwa Peter Sheng, Cincinnati, OH (US)

(*) Notice: Subject to any disclaimer, the term of this patent is extended or adjusted under 35 U.S.C. 154(b) by 0 days.

(21) Appl. No.: 13/466,384

(22) Filed: May 8, 2012

(65) Prior Publication Data

US 2013/0122035 A1 May 16, 2013

Related U.S. Application Data

(60) Provisional application No. 61/483,842, filed on May 9, 2011.

(51) Int. Cl.
| | |
|---|---|
| *A61K 36/06* | (2006.01) |
| *A61K 36/00* | (2006.01) |
| *A61K 36/539* | (2006.01) |
| *A61K 36/24* | (2006.01) |
| *A61K 36/344* | (2006.01) |
| *A61K 36/896* | (2006.01) |
| *A61K 36/41* | (2006.01) |
| *A61K 36/481* | (2006.01) |
| *A61K 36/748* | (2006.01) |
| *A61K 36/11* | (2006.01) |
| *A61K 36/17* | (2006.01) |
| *A61K 36/8966* | (2006.01) |
| *A61K 36/074* | (2006.01) |

(52) U.S. Cl.
CPC ............ *A61K 36/8966* (2013.01); *A61K 36/24* (2013.01); *A61K 36/344* (2013.01); *A61K 36/896* (2013.01); *A61K 36/41* (2013.01); *A61K 36/481* (2013.01); *A61K 36/748* (2013.01); *A61K 36/539* (2013.01); *A61K 36/11* (2013.01); *A61K 36/17* (2013.01); *A61K 36/074* (2013.01)
USPC ................ 424/195.15; 424/725; 424/741

(58) Field of Classification Search
None
See application file for complete search history.

(56) References Cited

U.S. PATENT DOCUMENTS

| | | | |
|---|---|---|---|
| 5,437,866 | A | 8/1995 | Sun |
| 6,911,221 | B2 | 6/2005 | Li |
| 7,005,146 | B2 | 2/2006 | Lee |
| 7,410,656 | B2 | 8/2008 | Aylward |
| 7,527,812 | B2 | 5/2009 | Hsieh |
| 7,569,234 | B2 * | 8/2009 | Liu et al. ............ 424/725 |
| 7,700,136 | B2 | 4/2010 | Cohen |
| 8,173,177 | B2 * | 5/2012 | Dao et al. ............ 424/725 |
| 2005/0136132 | A1 * | 6/2005 | Liu et al. ............ 424/725 |

FOREIGN PATENT DOCUMENTS

| | | | |
|---|---|---|---|
| CN | 101357202 A | * | 2/2009 |
| CN | 101502579 A | * | 8/2009 |
| CN | 101632819 A | * | 1/2010 |
| CN | 101670071 A | * | 3/2010 |
| CN | 101822806 A | * | 9/2010 |
| EP | 118616 A1 | * | 7/2001 |

OTHER PUBLICATIONS

Bai, C.A., et al., "Inhibitory effect of huangqi and dangshen extraction with pacilitaxel on metastasis and angiogenesis on mouse Lewis lung carcinoma model", Chin J Cell Mol Immunol, Apr. 2008, 24(4) 375-7.
Chang, W.H.,et al., "Different Effects of Baicalein, Baicalin, and Wogonin on Mitochondrial Function, Glutathione Content and Cell Cycle Progression in Human Hepatoma Cell Lines", Planta Medica, 2002, 68:128-32.
Cheung, J.Y., et al., "Polyphyllin D is a potent apoptosis inducer in drug-resistant HepG2 cells", Cancer Letters, 2005, 217:203-11.
Cho, W.C., et al., "In vitro and in vivo anti-tumor effects of Astragalus membranaceus", Cancer Letters, Jul. 8 2007, 252(1):43-54.
Deng, S., et al., "Synthesis of three diosgenyl saponins: dioscin, polyphyllin D, and balanitin 7", Carbohydr Res, 1999, 317:53-62.
El-Sayed, A.., et al., "*Catharanthus* Alkaloids. XXXIV. Catharanthamine, a New Antitumor Bisindole Alkaloid from *Catharanthus roseus*", J Nat Prod, 1981. 44(3):289-93.
Gao, Y., et al.,"Effects of Ganopoly (A *Ganoderma lucidum*Polysaccharide Extract) on the Immune Functions in Advanced-Staged Cancer Patients", Immunological Investigations , 2003, 32(3):201-15.
Gupta, S., et al., "Anticancer Activities of *Oldenlandia diffusa*", J Herb Pharmacother, 2004, 4(1):21-3.
Himes, R.H., "Interactions of the *Catharanthus* (Vinca) Alkaloids with Tubulin and Microtubules", Pharmacol Ther, 1991, 51(2):257-67.
Huang, D., et al., "Antitumor Activity of the Aqueous Extract from *Sedum sarmentosum* Bunge in Vitro", Cancer Biother Radiopharm, Feb. 2010, 25(1):81-8.
Jung, H., et al., "Anti-inflammatory, anti-angiogenic and anti-nociceptive activities of *Sedum sarmentosum* extract", J Ethnopharmacology, Feb. 2008, 116:138-43.
Kim, K.S., et al., "Antiproliferative Effect of *Scutellaria barbata* D. Don. on Cultured Human Uterine Leiomyoma Cells by Down-Regulation of the Expression of Bcl-2 Protein", Phtother Res, May 2008, 22(5):583-90.
Li, B., et al., "An improved synthesis of the saponin, polyphyllin D", Carbohydr Res, 2001, 331:1-7.

(Continued)

*Primary Examiner* — Chris R Tate
*Assistant Examiner* — Randall Winston
(74) *Attorney, Agent, or Firm* — Frost Brown Todd LLC

(57) ABSTRACT

An herbal composition and a method for treating cancer, especially for lung cancer, useful for enhancing the quality of life.

5 Claims, No Drawings

(56) References Cited

OTHER PUBLICATIONS

Man, S., et al., "Antitumor and antimetastatic activities of *Rhizoma paridis* saponins", Steroids, 2009, 74:1051-56.

McCulloch, M., et al., "Astragalus-Based Chinese Herbs and Platinum-Based Chemotherapy for Advanced Non-Small-Cell Lung Cancer: Meta-Analysis of Randomized Trials", J Clin Oncol., Jan. 20, 2006, 24(3):419-30.

Nonaka, Y., et al., "Effects of the Antlered form of *Ganoderma lucidum* onTumor Growth and Metastasis in Cyclophosphamide-Treated Mice", Bioscience, Biotechnology, and Biochemistry, 2008, 72(6):1399-1408.

Powell C.B., et al., "Aqueous extract of herba *Scutellaria barbatae*, a Chinese herb used for ovarian cancer, induces apoptosis of ovarian cancer cell lines", Gynecol Oncol, 2003, 91(2):332-40.

Rugo, H., et al., "Phase I trial and antitumor effects of BZL101 for patients with advanced breast cancer", Breast Cancer Res Treat, Sep. 2007, 105(1):17-28.

Sadava, D., et al., "Effect of *Ganoderma* on drug-sensitive and multidrug-resistantn small-cell lung carcinoma cells", Cancer Letters, May 2009, vol. 277, issue 2, 182-89.

Siu, F.M., et al., "Proteomic and transcriptomic study on the action of a cytotoxic saponin (Polyphyllin D): induction of endoplasmic reticulum stress and mitochondria-mediated apoptotic pathways", Proteomics, 2008, 8:3105-17.

Sonoda, M., et al., "Cytotoxic activities of flavonoids from two *Scutellaria* plants in Chinese medicine", J of Ethnopharm, Mar. 2004, 91:65-6.

Ueda, S., et al., "Baicalin induces apoptosis via mitochondrial pathway as prooxidant", Molecular Immunology, 2002, 38:781-91.

Van Der Heijden, R., et al., "The *Catharanthus* Alkaloids: Pharmacognosy and Biotechnology", Curr Med Chem, Mar. 2004, 11(5):607-28.

Wang, S., et al., "Angiogenesis and anti-angiogenesis activity of Chinese medicinal herbal extracts", Life Sci, 2004, 74(20):2467-78.

Weng, C.J., et al., "The in vitro and in vivo experimental evidences disclose the chemopreventive effects of *Ganoderma lucidum* on cancer invasion and metastasis", Clin Exp Metastasis, May 2010, 27(5) 361-9.

Wong, B., et al., "Inhibition of dexamethoasone-induced cytochrome P450-mediated mutagenicity and metabolism of aflatoxin B1 by Chinese medical herbs", Eur J Cancer Prev., Jul. 1993, 2(4):351-56.

Xiao, X., et al., "The antitumoral effect of Paris Saponin I associated with the induction of apoptosis through the mitochondrial pathway", Mol Cancer Ther, 2009, 8(5):1179-88.

Yang, L., et al., "Ursolic acid induces doxorubicin-resitant HepG2 cell death via the release of apoptosis-inducing factor", Caner Legg., 2010, 298(I):128-138.

Yin, X., et al., "Anticancer activity and mechanism of *Scutellaria barbata* extract on human lung cancer cell line A549", Life Sci, Sep. 2004, 75(18):2233-44.

Zhang , D., et al., "Inhibition of Cancer Cell Proliferation and Prostaglandin E2 Sysnthesis by *Scutellaria baicalensis*", Cancer Res, 2003, 63: 4037-43.

\* cited by examiner

HERBAL COMPOSITION FOR TREATING CANCER

CROSS REFERENCE TO RELATED APPLICATIONS

The present application hereby claims the benefit of the provisional patent application Ser. No. 61/483,842, filed on May 9, 2011, the disclosure of which is hereby incorporated by reference in its entirety.

BACKGROUND

About 222,500 new cases of lung cancer were diagnosed in the United States in 2010. Lung cancer accounted for about 28% of all cancer death in 2010 and it is the number one cause of death among all cancer types (Cancer Facts & Figures 2010 American Cancer Society). The five-year survival rate, standing at 17% (2002-2005), has improved very little in the past three decades.

Early diagnosis of lung cancer is difficult. For those with advanced stage lung cancer, chemotherapy has been the main-stay of treatment. But response is only modest and the median survival short, ranging from 8 to 13 months in clinical studies. In contrast, with best supportive care (without chemotherapy), survival is about 4-6 months. However, the true average survival may be less than the published data, as clinical trials typically enroll younger and medically fit patients, or in other words, an enriched population. It is also well known that the conventional chemotherapies can cause significant side effects and decrease quality of life.

In the past five years, two subsets of lung cancer patients have been identified for targeted therapy: 1) those who harbor an Epidermal Growth Factor Receptor (EGFR) mutation can be treated with Erlotinib, with a progression free survival of up to 9 months reported, and 2) those with ELM-4-ALK gene mutation can be effectively treated by Crizotinib. The challenge facing lung cancer doctors is that outside these 2 subsets, the majority of lung cancer patients, estimated to be 80-85% of the lung cancer population, have multiple mutated genes, and hence, multiple activated pathways. Therefore, the aforementioned targeted therapies have no or minimal therapeutic effects for them.

A recent French study looking specifically at stage IV elderly (age>70) lung cancer patients treated with either combination or single agent chemotherapy suggests that the elderly do benefit from aggressive treatment but they also experience more severe treatment related side effects. In the meanwhile, the cost of care for cancer patients has escalated quickly with the advent of new technology and very expensive targeted agents. Cost of cancer care now accounts for 5% of the total Medicare expenditure. There is a huge unmet need for safer, milder and more cost effective alternative treatment for advanced lung cancer.

Chinese herbal medicine, based on entirely different theory and practice, has helped patients with various diseases over the past thousands of years. Many cancer patients have sought Chinese herbal medicine for relief from the side effects of chemotherapy and radiation or to strengthen and balance their immune systems, in order to live better and longer.

Scientists in pharmaceuticals and biotechnology fields have studied different herbs for their anti-tumor activities and there is now abundant evidence that many herbs do have in-vivo and in-vitro anti-tumor effects.

As many of the currently available chemotherapy drugs come from natural products, and plants have been the basis of almost every new class of medication, it makes sense that plants can act as anticancer agents. Every herb has its own character, but only in combination will herbs have outstanding effects. Scientists often attempt to isolate one particular molecule or compound from the herbal composition, but in the Chinese herbal theory, the anticancer activity is due to the synergy between many of the compounds contained in the extract.

BRIEF SUMMARY

A composition of herbs and their extracts which is useful to treat lung cancer and which can also be used as a dietary supplement. The combination of the herb extracts improves lung cancer patients' condition and quality of life.

The composition may be provided in an ingestible form, such as powder, capsule, or tablet.

DETAILED DESCRIPTION

This herbal composition was created over a decade using the cumulative clinical experience of a medical oncologist who combines Eastern medicine and Western medicine in his practice. During this period of time, the components were changed several times in order to improve its efficacy, based not only on patients' feedback, but research into modern literature on traditional Chinese Medicine for potential cancer-fighting herbs. Initially, only *Scutellaria barbata* and *Oldenlandia diffusa* were combined. Due to lack of efficacy, *Scutellaria baicalensis* and *Bulbus fritillariae* were added. Subsequently, other herbs were added or deleted at different time points. In the past three years, extracts of *Ganoderma lucidum* were incorporated to strengthen its anti-cancer potency and spectrum which then completed the current composition. Extracts of *Ganoderma lucidum, Sedum sarmentosum*, and *Catharanthus roseus* were incorporated to strengthen its anti-cancer potency and spectrum.

Historically, traditional Chinese herbal medicine formulas comprise many components, usually extract of raw herbs with each one present in very small quantity. The belief is that there is synergism among different components. One advantage of this kind of formulation is to avoid excessive toxicity when any one component is given in large quantity. This is in sharp contrast to western medicine where a pharmacologically active molecule is given in a large dose, often a maximally tolerated dose (MTD), to target one physiologic endpoint. The approach with multiple herbal ingredients may be analogous to metronomic chemotherapy which has been extensively studied in the past 10 years. Through constant administration of a low dose of chemotherapeutic agents such as etoposide or cyclophosphamide, often in combination with anti-inflammatories such as celecoxib, and antiangiogenic agents such as thalidomide, some heavily pretreated patients with cancer refractory to chemotherapy may achieve disease stabilization lasting for a long time. The metronomic approach certainly deviates from the usual dose-response curve in pharmacology and the toxicity profile is usually favorable.

This herbal composition may have potential either as an adjunctive therapy to the standard treatment available right now or an alternative to those who do not wish to receive chemotherapy or are poor candidates for chemotherapy.

Since there are up to ten herbs present in the composition, each in small quantities, the possibility of significant herb-drug interactions is small. However, their combination is able to produce a synergistic effect that is greater than each of the herbs individually. There have not been any observed serious adverse reactions from using the herbal composition.

Except for one patient with prolonged remission, the most commonly seen "positive outcome" with the herbal composition is stable disease (SD) for a period of six months or longer, rather than partial response (PR). Most patients did notice improved quality of life (QOL). There is a strong suggestion that the herbal composition did help many patients live significantly longer given their near-terminal status of their disease when they began herbal therapy.

Proof of efficacy of the herbal composition was tested in a cell line study. In the study, a water solution of the herbal composition demonstrated inhibitory activity in CL1-0 and A549 lung cancer cells, Bx/P3 pancreatic cancer cells, and Panc-1 pancreatic cancer cells.

Clinical observation has shown that the herbal composition is very safe with oral administration. Patients have only an occasional incidence of mild nausea, diarrhea, or abdominal bloating. Once dosage is reduced and given after meals, side effects are usually alleviated. The herbal composition has been given concurrently with Erlotinib and chemotherapy. Based on a small number of cases, there appears to be no drug-herb interaction although no pharmacokinetic study has been conducted. Patients using concurrent therapy have all done exceptionally well, living much longer than expected.

The cost of cancer care, which now accounts for 5% of total Medicare expenditure, has escalated quickly in recent years because of newer drugs and technology. In the meanwhile, chemotherapy can be associated with serious side effects, especially beyond the first line setting. There is an urgent need for safer, milder and more cost-effective treatment options.

The herbal composition relates to a mixture of Chinese herbs having anticancer effects and immune strengthening properties. In one embodiment the herbal composition comprises *Catharanthus roseus* and *Sedum sarmentosum*. In another embodiment the herbal composition additionally comprises Scutellaria barbata. In another embodiment the herbal composition additionally comprises *Oldenlandia diffusa*. In another embodiment the herbal composition additionally comprises *Rhizoma paridis*. In another embodiment the herbal composition additionally comprises *Scutellaria baicalensis*. In another embodiment, the composition comprises a mixture of *Catharanthus roseus, Sedum Sarmentosum, Rhizoma paridis*, and *Scutellaria baicalensis*.

In one embodiment the herbal composition comprises *Catharanthus roseus, Sedum sarmentosum, Scutellaria barbata, Oldenlandia diffusa, Rhizoma paridis, Scutellaria baicalensis, Ganoderma lucidum, Astragalus membranaceus, Codonopsis pilosula*, and *Bulbus fritillariae*.

*Catharanthus roseus*, also known as Medagascar Periwinkle, is widely cultivated and is naturalized in subtropical and tropical areas of the world. In traditional Chinese medicine as well as elsewhere in the world, extracts from it have been used to treat a variety of diseases such as diabetes mellitus, malaria, and Hodgkin's disease. Vincristine and vinblastine, two alkaloids extracted from the plant, have been used in the treatment of leukemia. Vinca alkaloids target intracellular tubulin, the protein monomer of microtubules, leading to disruption of microtubules, thus inhibiting cell mitosis and cell growth. Although vincristine and vinblastine are associated with some potentially serious side effects including myelosuppression and neuropathy, tincture of vinca can be used safely when given orally in small quantity (for instance, 1 ml twice or three times a day) as the absolute levels of vincristine and vinblastine present in tincture are considered far too low. Anti-cancer activity of crude extracts of *Catharanthus* against numerous cell types can be demonstrated in vitro, probably due to a synergy among many different vinca alkaloids. Crude decoction of *Catharantus* also demonstrated moderate anti-angiogenesis effect in vitro. While extracts of vinca have been used in traditional medicine, vinca is known widely to be toxic and extracts of vinca are thus also considered to be toxic.

Vinca alkaloids have been used by oncologists for treatment of a variety of solid tumors and leukemia. Clinically, the combination of cisplatin and vinorelbine (an alkaloid derived from vinca) is considered the most active adjuvant chemotherapy regimen in early stage lung cancer after surgical resection.

*Sedum Sarmentosum* (SS) has been used in China as a folk remedy for conditions such as snake bites, sore throat, carbuncles, or viral hepatitis. Recent studies in vitro and in animal models suggest that aqueous extract of SS has anti-apoptotic and anti-angiogenic properties, in addition to its well-known anti-inflammatory effect. Another cell culture study demonstrated decreased nitric oxide production by macrophages.

*Scutellaria barbata*, also known as Ban Zhi Lian, is used as an anti-inflammatory and cancer fighting herb in China. Frequently used in combination with *Oldenlandia diffusa*, *Scutellaria Barbata* found its usage in cancer of lung, and digestive tract including hepatoma in Chinese folk medicine.

In studies involving different cancer cell lines and animal models, *S. barbata* has been shown to upregulate the apoptotic pathway and downregulate the survival pathway. Others reported the anti-proliferative property of *S. bartata* using a cancer cell line, HL-60. Extracts of *S. barbata* has finished a phase I clinical study and data has been presented at Annual Society of Clinical Oncology (ASCO) meeting in 2007. Some patients with refractory breast cancer saw stabilization of their diseases for more than 180 days.

*Oldenlandia diffusa. Oldenlandia diffusa* and *Scutellaria barbata* have been used in tradition Chinese medicine for treating liver, lung, and rectal tumors. *Oldenlandia diffusa* is used in China and East Asia to "clear heat and to eliminate toxins," and has also been shown to exert anti-cancer and chemopreventive effects when studied both in vitro and in animal models.

*Oldenlandia diffusa* extract has effectively inhibited the growth of eight cancer cell lines and induced apoptosis. There was also significant inhibition of lung metastases in the animal model with no noticeable adverse effects.

Several mechanisms of action have been cited including a caspase-dependent apoptosis, immuno-modulating activity through stimulation of the immune system and inhibition of metastasis. Two active ingredients, oleanolic and ursolic acids have been isolated from *Oldenlandia diffusa* and both demonstrated cytotoxicity.

*Rhizoma paridis*, also known as Chong Lou, is another Chinese herb that has received a lot of attention in recent years. It is used extensively in traditional Chinese medicine as a natural antibiotic, and it has been incorporated in a number of anticancer formulas.

The active components, PSI and PSVI have been approved for cancer therapy in China because of their potential involvement in the suppression of tumor growth. Synthetic PSI has also been shown to render cytotoxic effects against non-small-cell lung cancer and hepatocellular carcinoma cell line.

A number of possible explanations have been offered based on in vitro and in vivo studies for its activity:

1) inducing cancer cell apoptosis, probably through the mitochondrial pathway
2) anti-metastatic activities through down regulation of Matrix Metalloproteinaces (MMP)

3) bypassing multi-drug resistance (MDR), probably by down-regulation of the expression of chemotherapeutic agent resistance-related genes 4) synergistic with a variety of chemotherapeutic drugs.

*Scutellaria baicalensis* (Huang Qin). The link between inflammation and cancer is well known. Chronic inflammation contributes to the development of cancer and cancer progression. Extract of Huang Qin has shown strong anti-inflammatory activities in recent research, such as suppression of proliferation cell nuclear antigen, COX-2 expression and $PGE_2$ synthesis. Huang Qi is also capable of blocking nuclear factor Kappa B (NF-KB) activation, a potent mediator in inflammatory pathway.

Several studies have indicated that extracts of Huang Qin have growth inhibitory effects on a number of human cancers. Research has shown that extracts of Huang Qin greatly inhibited the growth of lung cancer cell line A549. Similar to many other anti-cancer herbs used in traditional Chinese medicine, Huang Qin can induce cell apoptosis in cancer cell lines. Different active components, Wognin, Baicalin, and others, most likely work synergistically to the effect.

*Ganoderma lucidum* (GL), also known as Ling Zhi, or Reishi, has become popular in the past two decades among cancer survivors.

Recent in vitro and animal studies have suggested that *Ganoderma lucidum* exhibits anticancer activity. Multiple anticancer mechanisms have been demonstrated. In one study with highly invasive breast cancer cells MDA-MB-231, GL suppressed cancer cells motility, modulated the metastatic behavior and inhibited cell adhesion, cell migration and cell invasion.

Another study suggested enhanced immune response in patients with advanced stage cancer, as demonstrated by the mean Natural Killer Cell (NK) activity. With regards to lung cancer research, one in vitro study showed that extracts of several species of *Ganoderma* are cytotoxic to both drug-sensitive and drug-resistant small cell lung cancer (SCLC) cells, are pro-apoptotic and can reverse resistance to chemotherapeutic drugs.

Another study using a mouse model demonstrated improved anti-tumor an anti-metastatic effects, when mice were treated with a combination of *Ganoderma* extract and cyclophosphamide. The result was attributed to the modulatory effects of *G. Lucida* on both cellular and humoral immunity.

*Astragalus membranaceus* (Huang Qi). Huang Qi is one of the main medical herbs in traditional Chinese medicine. According to traditional Chinese medicine guidelines, Huang Qi generates Qi or the life force, promotes functions of lung, treats lung weakness, helps digestion, improves circulation, and decreases sweating. Huang Qi is commonly used in combination with other herbs.

Modern research has confirmed its immune-potentiating effects. McCulloch et al. performed a meta-analysis in which 34 randomized studies involving 2,815 patients were analyzed. When Huang Qi based herbal medicine was used in conjunction with platinum compounds, tumor response and patients' performance status improved, and chemo induced toxicity reduced. Another review from Cochrane database showed similar findings. In addition, in one study using mouse Lewis Lung cancer model when extracts of Huang Qi and Dang Shen were combined with Paclitaxel, better anti-angiogenesis and anti-metastasis as well as improved survival were demonstrated when compared to paclitaxel alone.

*Codonopsis pilosula* (Dang Shen). Dang Shen, long regarded as a tonic herb, has been used to treat chronic fatigue and to improve immune system. Often referred to as a poor man's Ginseng, Dang Shen is used as an adaptogen by modern day herbalists.

*Bulbus fritillariae* (Bei Mu). Bei Mu has long been an essential element of many traditional Chinese herbal formulas to treat a wide variety of lung disorders. It has antitussive property and can also rid the body of phlegm. It works best for patients with Yin energy deficiency, i.e. those with low parasympathetic tone with clinical manifestations including low grade fever, thirst sensation, palpitation, dry cough, mental irritability, sleep disturbance due to early awakening, night sweats, etc.

In summary, many basic anti-cancer mechanisms utilized by antineoplastic drugs and modern targeted therapy are also shared by herbs in the herbal composition such as induction of cancer cell apoptosis and anti-proliferative, antiangiogensis, antimetastasis etc, at least when tested in cell lines or in animal models.

In one embodiment the herbal composition is an aqueous solution of herbal extracts. In another embodiment the herbal composition is a mixture of the herbal extracts in powdered form. The extracts may be aqueous or organic solvent extracts of the herbs. In one embodiment the extracts are an alcohol extract of the herb. The extracts may be in liquid or powdered form. In one embodiment the extracts are powders.

An extract refers to the residue of soluble solids obtained after an herb, or selected part thereof is for example chopped, crushed, pulverized, minced, or otherwise treated to expose maximum surface area and placed in intimate contact with a liquid, usually, but not necessarily, under conditions of agitation and elevated temperature. Then, after a period of time under these conditions the mixture is filtered to remove solids and the liquid is removed by, for example but not limitation, evaporation or freeze drying. The liquid used to obtain an extract may be water or an organic solvent, for example, without limitation, an alcohol such as methyl, ethyl or isopropyl alcohol, a ketone such as acetone or methyl ethyl ketone (MEK), an ester such as ethyl acetate, an organochlorine compound such as methylene chloride, chloroform or carbon tetrachloride, a hydrocarbon such as pentane, hexane, toluene, or benzene and the like. An extract may also be obtained by using a combination of these solvents with or without water.

The herbal composition may be a combination of aqueous or ethanol extracts of the ten herbs listed above. The weight ratios of any two dried herbal extracts may range from 1:10 to 10:1. In one embodiment, the weight ratio is 1:1. The composition may be in pill, tablet, capsule, liquid, or powder form. The capsules and powder mixture may be mixed in water before oral administration.

The dosage of the herbal composition varies depending upon the cancer type, the stage of disease, and the individual patient. In general, the amount of herbal composition administered to a human patient is from about 2 to 15 grams per day. In some embodiments, the effective dose is 4 to 12 grams per day. In another embodiment, the dose is about 5 to about 8 grams per day. In another embodiment, the dose is about 5 to about 6 grams per day. In another embodiment, the dose is about 6 to about 8 grams per day in two divided doses after meals. The does may be divided into 2 or 3 treatments per day.

A therapeutically effective amount refers to that amount of an extract or combination of extracts which has the effect of reducing the size of the tumor; inhibiting (that is, slowing to some extent, preferably stopping) tumor metastasis; inhibiting to some extent (that is slowing to some extent, preferably stopping) tumor growth; relieving to some extent (or preferably eliminating) one or more symptoms associated with cancer; stabilizing the growth of the tumor; extending the time to disease progression; improving overall survival; or increasing the quality of life.

A pharmaceutical composition refers to a mixture of the herbal composition with other chemical components, such as physiologically acceptable carriers and excipients. The purpose of a pharmacological composition is to facilitate administration of an extract or extracts of this invention to patient.

A physiologically acceptable carrier refers to a carrier or diluent that does not cause significant irritation to an organism and does not abrogate the biological activity and properties of the administered composition.

An excipient refers to an inert substance added to a pharmaceutical composition to further facilitate administration of the herbal composition. Examples, without limitation, of excipients include calcium carbonate, calcium phosphate, various sugars and types of starch, cellulose derivatives, gelatin, vegetable oils, and polyethylene glycols.

In one embodiment, a method for treating cancer comprises administering an effective amount of an aqueous or organic solvent extract of *Catharanthus roseus* and *Sedum sarmentosum*.

The herbal composition may be administered to a patient as a "tea," without combination with any other substances or further manipulation; it may be administered as a pharmaceutical composition where the herbal composition is mixed with suitable carriers or excipient. In treating a patient exhibiting a disorder of interest, a therapeutically effective amount of the herbal composition is administered.

When the herbal composition is administered without combination with any other substances, the composition may be encased in a suitable capsule, such as a gelatin capsule. When administered in admixture with other excipients, adjuvants, binders, diluents, disintegrants, etc., the herbal composition may be compressed into a capsule or caplet in a conventional manner that is well-known in the art.

The herbal composition may be useful for treating non-small cell lung cancer, ovarian cancer, neuroendocrine cancer, acute myeloid leukemia, head and neck cancer, non-Hodgkin's lymphoma, melanoma, breast cancer, gastric cancer, pancreatic cancer, cancer of the uterus, esophageal cancer, thyroid cancer, and glioblastoma.

In one embodiment the herbal composition may be administered to a human undergoing chemotherapy. In another embodiment, the herbal composition may be administered to a human that is not undergoing chemotherapy.

There is a huge unmet need for patients with advanced cancers, especially lung cancer. Even though modest progress has been made in recent years in chemotherapy for lung cancer, the average progression-free survival (PFS) is in the order of five or six months. Only limited options exist in the second line setting where the risk/benefit ratio is usually not favorable, with response rate typically less than 10%.

In one embodiment the herbal composition may be useful for the treatment of lung cancer. In another embodiment the herbal composition may be useful for the treatment of cancer of the endometrium or cancer of the esophagus.

About 222,500 new cases of lung cancer were diagnosed in the United States in 2010. Lung cancer accounts for about 28% of all cancer death in 2010 and it is the number one cause of death among all cancer types (Cancer Facts & Figures 2010 American Cancer Society). The five year survival rate, standing at 17% (2002-2005), has improved very little in the past three decades.

Early diagnosis of lung cancer is difficult. For those with advanced stage lung cancer, chemotherapy has been the mainstay of treatment. But response is only modest and the median survival short, ranging from 8 to 13 months in clinical studies. In contrast, with the best supportive care (without chemotherapy) survival is about 4-6 months. However, the true average survival maybe less than the published data, as clinical trials typically enroll younger and medically fit patients or, in other words, an enriched population. It is also well known that the conventional chemotherapies can cause significant side effects and decrease quality of life.

Targeted therapy for those who harbor a dominant oncogenic driver, such as EGFR mutation or ELM-4-ALK, may produce longer remission, up to 9 months. However, only an estimated 15% of the lung cancer patients have such a mutation.

An improvement in the quality of life is an improvement of performance status (PS). One of the more popular methods of measuring the PS is though the ECOG (Eastern Cooperative Oncology Group) score. The ECOG ranges from 0 to 5, with 0 denoting perfect health and 5 death.

0—Asymptomatic. (Fully active, able to carry on all pre-disease activities without restriction).

1—Symptomatic but completely ambulatory. (Restricted in physically strenuous activity but ambulatory and able to carry out work of a light or sedentary nature. For example, light housework, office work).

2—Symptomatic, <50% in bed during the day. (Ambulatory and capable of all self care but unable to carry out any work activities. Up and about more than 50% of waking hours).

3—Symptomatic, >50% in bed, but not bedbound. (Capable of only limited self-care, confined to bed or chair 50% or more of waking hours).

4—Bedbound. (Completely disabled. Cannot carry on any self-care. Totally confined to bed or chair).

While the present disclosure has illustrated by description several embodiments and while the illustrative embodiments have been described in considerable detail, it is not the intention of the applicant to restrict or in any way limit the scope of the appended claims to such detail. Additional advantages and modifications may readily appear to those skilled in the art.

EXAMPLES

The usefulness of the herbal composition is shown in different clinical settings by the following selected case examples, with many patients being poor candidates for standard conventional treatment, and some even being terminally ill.

Example 1

A 60 year-old female, a former smoker, with stage IV adenocarcinoma of the lung (metastatic disease confined to the lungs), had been stable on maintenance chemotherapy, a single agent Pemetrexed. She chose to have a chemotherapy holiday and went on this herbal composition. Her disease stabilized for 6 months. Repeat imaging later showed progression of one lung nodule from 6 to 12 mm. She remained asymptomatic clinically with better quality of life, but chose to move on to other treatment. The performance score (PS) was initially 0 and remained at 0.

Example 2

A 72 years old female with stage IV lung cancer, after 18 months of chemotherapy, her blood counts became low and she felt exhausted. She discontinued chemotherapy and sought alternative therapy. She was referred to us by her medical oncologist.

Her performance status improved and quality of life improved dramatically after she started the herbal composition. Two months later, she was able to cook Thanksgiving dinner for her family of 20, with some assistance. Six months later, her repeat scan showed decreased tumor activity (decreased SUV number on CT/PET scan). She lived another 15 months on the herbal supplements only and during the 15 months she did not go to the hospital for any condition. The PS was initially 3 and increased to 0.

Example 3

A 58 year old white male, never smoked, was diagnosed as having bronchiole-alveolar cancer of lung (now called adenocarcinoma) in 2004. He did not respond to initial chemotherapy, but did respond to Erlotirib (Tarceva) for about one year. When his cancer progressed again, he went on this herbal composition as there were no more effective treatment options. Although he only used herbs intermittently, he remained in remission for five years, only to have recurrence diagnosed in 2011. He received more chemotherapy and restarted herbal therapy too. Currently, he is living a good quality life. The PS increased from 3 to 0 for several years, then the cancer returned.

Example 4

An 80 year old white female came to Cincinnati after a diagnosis of a stage III cancer of lung. She tolerated concurrent chemotherapy (weekly low dose) and radiation poorly. She discontinued the chemotherapy after just two weeks of treatment. She did manage to finish chest radiotherapy. She became very weak upon the completion of the planned treatment. With herbal therapy, she gradually regained her strength. She then moved back to New York to live in her own home by herself, as her quality of life improved significantly. She has remained cancer free for two and a half years. The PS increased from 3 to 1-0.

Example 5

A 65 year old male smoker with stage IV lung adenocarcinoma was referred to the local hospice in December 2011 because of cancer progression and lack of effective treatment, about one year after initial diagnosis. He started this herbal therapy and his weight stabilized and quality of life improved immediately. He expired three months later, but had remained active till just a few days before his death from spinal cord compression and its complications. The PS increased from 2 to 1 in less than 3 months.

Example 6

A 66 year old male smoker developed stage IV disease, right adrenal and lymph node metastasis, two years after resection of an earlier stage cancer of lung despite post-op adjuvant chemotherapy. Due to prior spinal cord injury, paraparesis and lack of systemic symptoms, he preferred to postpone systemic chemotherapy for as long as it is possible. He remained clinically stable, for months after beginning herbal therapy, although his repeat imaging tests showed mild interval disease progression. The PS was difficult to assess because it was affected by the prior spinal cord injury; it is probably best characterized as unchanged.

Example 7

A 65 year old white female with advanced lung cancer predominantly in lungs presented with extreme shortness of breath. She was told by her physician to be admitted to hospice for terminal care. After starting on herbal composition, as well as Erlotinib (Tarceva) and Zometa for hypercalcemia, her general conditions gradually improved. She now lives a very active lifestyle, having just returned from a 5-week trip to a foreign country. Her tumor marker, CEA, has decreased to 30 from 169 one year ago. Her cancer was one that did not have an EGFR mutation. The PS increased from 3 to 0. She is now back to full time farming, doing very laborious work; a dramatic recovery. Not all of the improvement may be credited to the herbal composition because she also took Tarceva, which is an oral drug. However, taking Tarceva alone should not have resulted in a dramatic response because she does not have the gene mutation. (EGFR)

Example 8

A 62 year old male with cancer of esophagus who developed metastatis six months after resection of the primary lesion. He failed first line chemotherapy, and began taking this herbal composition. He has done well for about four months and feels well clinically. Two months after he began herbal therapy, he did attempt a second line chemotherapy with Irinotecan which caused severe diarrhea. Irinotecan was discontinued immediately. The PS stayed at 1.

Example 9

A 63 year female with history of cancer of the endometrium presented with rising CA-125, two years after initial surgery and adjuvant chemotherapy. She started this herbal composition and her CA-125 returned to within normal range for about one year. She is still continuing the herb and remains asymptomatic although her CA-125 is beginning to rise. The PS stayed at 0.

Example 10

In ex vivo chemosensitivity testing provided by Rational Therapeutics based in Long Beach, Calif., the aqueous herbal composition induced apoptosis, necrosis, and autophagy in a number of tumor types. The herbal composition was tested on various actual cancer cells including: non-small cell lung cancer, ovarian cancer, neuroendocrine cancer, acute myeloid leukemia, head and neck cancer, non-Hodgkin's lymphoma, melanoma, breast cancer, gastric cancer, pancreatic cancer, cancer of the uterus, esophageal cancer, thyroid cancer, and glioblastoma.

Two grams of the dried herbal preparation were weighed and dissolved in 25 ml of sterile saline. The mixture was stirred for 30 minutes. Solid material was removed by density centrifugation and the remaining supernatant was sterile filtered. The working solution at 80 mg/ml was added at a 1:10 dilution and then serially diluted at 1:2. The working concentration ranges consisted of 8 mg/ml; 4 mg/ml; 2 mg/ml; 1 mg/ml; 0.5 mg/ml. Cell death is measured based on morphologic and metabolic measurements to assess the response. The response curves are interpolated to provide $IC_{50}$ values. The data shows that the herbal composition is cytotoxic to numerous human cancers.

| Testing Results | | | |
|---|---|---|---|
| Cancer Cell | Average $IC_{50}$ (mg/ml) | Z-Score | Count |
| Acute Myeloid Leukimia | 1.2 | −4.97 | 1 |
| Head and Neck | 1.5 | −4.15 | 1 |
| Non-small cell lung cancer | 1.575 | −3.94 | 4 |
| Non-Hodgkin's Lymphoma | 2.2 | −2.23 | 1 |
| Melanoma | 2.4 | −1.68 | 1 |
| Breast | 2.5 | −1.40 | 1 |
| Ovarian | 2.6125 | −1.09 | 8 |
| Gastric | 2.7 | −0.85 | 1 |
| Uterus | 3.2 | 0.52 | 1 |
| Esophagus | 3.4 | 1.07 | 1 |
| Neuroendocrine | 3.78 | 2.11 | 5 |
| Thyroid | 4.6 | 4.37 | 1 |
| Pancreas | 4.75 | 4.78 | 2 |
| Glioblastoma | 8 | 13.71 | 1 |

Example 11

The $IC_{50}$ of the herbal composition was measured for various lung and pancreatic cancer cells as shown in the table below.

| Measured IC$_{50}$/72 hours for lung and pancreatic cancer cells | |
|---|---|
| Lung, pancreatic cancer cells | IC$_{50}$/72 h |
| A549 lung cancer cells | 120 µg/ml |
| NCI-H460 lung cancer cells | 900 µg/ml |
| Bx/P3 pancreatic cancer cells | 260 µg/ml |
| Panc-1 pancreatic cancer cells | 240 µg/ml |
| Panc-1 pancreatic cancer cells Gemcitabine resistance (100 µg/ml) | 400 µg/ml |

What is claimed is:

1. A method for treating cancer comprising administering an effective amount of a composition to a person in need thereof,
wherein the composition comprises an aqueous or organic solvent extract of *Catharantus roseus, Sedum sarmentosum, Scutellaria barbata, Oldenandia diffusa, Rhizoma paridis, Scutellaria baicalensis, Ganoderma lucidum, Astragalus membranceus, Codonopsis pilosula* and *Bulbus fritillariae.*

2. The method of claim 1, wherein the cancer is lung cancer.

3. The method of claim 1, wherein the weight ratios of the extracts range from 1:10 to 10:1.

4. The method of claim 1, wherein the weight ratios of the aqueous or organic solvent extract of *Catharantus roseus, Sedum sarmentosum, Scutellaria barbata, Oldenandia diffusa, Rhizoma paridis, Scutellaria baicalensis, Ganoderma lucidum, Astragalus membranceus, Codonopsis pilosula* and *Bulbus fritillariae,* are about 1:0.75:1:1:1:1:1:1:1:1, respectively.

5. The method of claim 1, wherein the composition is administered in a dose range of about 6 to about 8 grams per day in two to three divided doses.

* * * * *